(12) United States Patent
Shigemaru

(10) Patent No.: US 10,466,226 B2
(45) Date of Patent: Nov. 5, 2019

(54) MEASURING DEVICE

(71) Applicant: YAMASHIN-FILTER CORP., Kanagawa (JP)

(72) Inventor: Daichi Shigemaru, Kanagawa (JP)

(73) Assignee: YAMASHIN-FILTER CORP., Kanagawa (JP)

(*) Notice: Subject to any disclaimer, the term of this patent is extended or adjusted under 35 U.S.C. 154(b) by 87 days.

(21) Appl. No.: 15/823,963

(22) Filed: Nov. 28, 2017

(65) Prior Publication Data

US 2018/0080862 A1 Mar. 22, 2018

Related U.S. Application Data

(63) Continuation of application No. PCT/JP2016/066165, filed on Jun. 1, 2016.

(30) Foreign Application Priority Data

Jun. 12, 2015 (JP) ................. 2015-118980

(51) Int. Cl.
  *G01N 33/28* (2006.01)
  *G01N 15/14* (2006.01)
  (Continued)

(52) U.S. Cl.
  CPC ......... *G01N 33/2888* (2013.01); *G01N 15/06* (2013.01); *G01N 15/14* (2013.01);
  (Continued)

(58) Field of Classification Search
  CPC ........... G01N 15/14; G01N 2015/0693; G01N 2015/0053; G01N 2015/0057;
  (Continued)

(56) References Cited

U.S. PATENT DOCUMENTS 4,260,258 A * 4/1981 Rose .................. G01N 15/1434
  250/573
4,739,177 A 4/1988 Borden
(Continued)

FOREIGN PATENT DOCUMENTS

EP 231542 A2 8/1987
JP S61-189251 U 11/1986
(Continued)

OTHER PUBLICATIONS

International Search Report issued in PCT/JP2016/066165 dated Sep. 6, 2016, with translation (5 pages).
(Continued)

*Primary Examiner* — Paul M. West
(74) *Attorney, Agent, or Firm* — Nakanishi IP Associates, LLC

(57) ABSTRACT

A measuring device can be used under high pressure and can measure impurity particles contained in a hydraulic oil with high accuracy. A flow path hole opening on two facing surfaces of a housing has flat side surfaces. A cavity opens on the side surface, and a cavity opens on the side surface. Light emitted from a light irradiating section irradiates a hydraulic oil flowing in the flow path hole, via a cell disposed in the cavity in a direction substantially orthogonal to a center axis. Light passing through the hydraulic oil is received by a light receiving section via a cell disposed in the cavity opening on the side surface.

8 Claims, 9 Drawing Sheets

(51) Int. Cl.
*G01N 21/84* (2006.01)
*G01N 15/06* (2006.01)
*G01N 21/03* (2006.01)
*G01N 21/85* (2006.01)
*G01N 15/00* (2006.01)
*G21K 5/00* (2006.01)

(52) U.S. Cl.
CPC ......... *G01N 21/0317* (2013.01); *G01N 21/84* (2013.01); *G01N 21/85* (2013.01); *G01N 2015/0053* (2013.01); *G01N 2015/0057* (2013.01); *G01N 2015/03* (2013.01); *G01N 2015/0687* (2013.01); *G01N 2015/0693* (2013.01); *G01N 2021/8405* (2013.01); *G01N 2021/8557* (2013.01); *G21K 5/00* (2013.01)

(58) Field of Classification Search
CPC ............... G01N 15/0205; G01N 21/85; G01N 2021/8557; G01N 2021/8405; G01N 33/2888
See application file for complete search history.

(56) References Cited

U.S. PATENT DOCUMENTS 4,781,459 A 11/1988 Suzuki
RE33,213 E 5/1990 Borden

FOREIGN PATENT DOCUMENTS

| | | |
|---|---|---|
| JP | S62-123549 U | 8/1987 |
| JP | S62-215843 A | 9/1987 |
| JP | S63-095341 A | 4/1988 |
| JP | 2009-162712 A | 7/2009 |
| JP | 2013-142626 A | 7/2013 |

OTHER PUBLICATIONS

Written Opinion of International Searching Authority issued in PCT/JP2016/066165 dated Sep. 6, 2016 (4 pages).
Masanori Ishizuka, "The Cleanliness Sensor of Hydraulic Oil," Journal of the Japan Fluid Power System Society, issued on Mar. 2015 (3 pages).

* cited by examiner

US 10,466,226 B2

MEASURING DEVICE

CROSS-REFERENCE TO RELATED APPLICATIONS

The present application is a continuation application of International Patent Application No. PCT/JP2016/066165 filed on Jun. 1, 2016, which claims priority to Japanese Patent Application No. 2015-118980 filed on Jun. 12, 2015, the entire contents of which are incorporated by reference.

TECHNICAL FIELD

The present invention relates to a measuring device.

BACKGROUND ART

Patent Document 1 discloses an impurity particles measuring device that includes a light emitting diode emitting light to a pipe through which oil (hydraulic oil) or the like flows, two light receiving elements arranged apart from each other in a direction of the flow path of a fluid and detecting light transmitted through a flow path by the light emission, and a detecting section detecting an amount of impurity particles flowing in the flow path from differences in respective outputs of the light receiving elements, and that measures impurity particles, such as oil dust contained in the hydraulic oil and the like.

CITATION LIST

Patent Document

Patent Document 1: JP 2013-142626 A

The invention described in Patent Document 1 uses, as the pipe, a glass tube made from an optically transparent material, such as glass. Unfortunately, even in a case where the glass tube is made from, for example, high-strength sapphire glass, an increased pressure of the hydraulic oil or the like flowing in the pipe may generate a crack or the like in the glass tube and may thus increase a measurement error.

SUMMARY OF INVENTION

One or more aspects of the present invention are directed to a measuring device that can be used under high pressure and can measure impurity particles contained in a hydraulic oil with high accuracy.

A measuring device according to an aspect of the present invention includes, for example: a housing having two surfaces facing each other, the housing being provided with a flow path hole, a first cavity, and a second cavity, the flow path hole opening on the two facing surfaces and having a first side surface and a second side surface facing each other, the first cavity having one end opening on the first side surface, the second cavity facing the first cavity across a center axis of the flow path hole and having one end opening on the second side surface; a first cell disposed in the first cavity, made from a transparent material, and having a substantially cylindrical shape, both ends surfaces of the first cell being flat surfaces; a second cell disposed in the second cavity, made from a transparent material, and having a substantially cylindrical shape, both ends surfaces of the second cell being flat surfaces; a light emitting section configured to irradiate a hydraulic oil flowing in the flow path hole with light via the first cell in a direction substantially orthogonal to the center axis; and a light receiving section disposed facing the light irradiating section across the first cell, the flow path hole, and the second cell. The first cavity and the second cavity have centers substantially coinciding with an optical axis being a center of light emitted from the light irradiating section.

In the measuring device according to an aspect of the present invention, the flow path hole having the center axis orthogonal to the two facing surfaces and having the first side surface and the second side surface facing each other is formed in the housing. This configuration enables the measuring device to be used under high pressure.

In the measuring device according to an aspect of the present invention, light emitted from the light emitting section irradiates the hydraulic oil flowing in the flow path hole, via the first cell disposed in the first cavity opening on the first side surface in the direction substantially orthogonal to the center axis of the flow path hole, and is received by the light receiving section disposed facing the light emitting section across the first cell, the flow path hole, and the second cell disposed in the second cavity opening on the second side surface. This configuration enables measurement of impurity particles contained in the hydraulic oil to be highly accurate.

Here, the flow path hole may have both ends shaped into a round cavity; and the flow path hole may have such a tapered shape that a shape in a plane substantially orthogonal to the center axis changes from the round cavity to a long cavity having two sides substantially orthogonal to the optical axis. This configuration stabilizes the flow of the hydraulic oil flowing in the measurement hole, resulting in an increase in the measurement accuracy.

Here, the first side surface and the second side surface may be flat surfaces; an end surface of the first cell disposed in the first cavity and the first side surface may be substantially in the same plane; and an end surface of the second cell disposed in the second cavity and the second side surface may be substantially in the same plane. This configuration can reduce generation of swirls.

Here, the tapered shape may be formed such that an angle formed by two lines facing across the center axis is approximately 60 degrees. This configuration prevents swirls from being generated in the hydraulic oil flowing in the measurement hole, resulting in a stable flow.

Here, a distance between the first side surface and the second side surface may be smaller than a length of the first side surface and the second side surface in the direction substantially orthogonal to the center axis. This configuration shortens the distance between the light emitting section and the light receiving section, resulting in an increase in the measurement accuracy.

Here, the first cell and the second cell each may include a main portion having a substantially cylindrical shape and a flange portion formed at an end of the main portion and having a substantially thick circular plate shape with a diameter greater than a diameter of the main portion. Sealing members may be disposed between the first cavity and the main portion and the second cavity and the main portion. The housing may be provided with first and second pressing members. The first and second pressing members are configured to press the first and second cells, respectively. With the pressing members being disposed in the housing, end surfaces, on the main portion side, of the flange portions may be pressed against the housing. This configuration can improve the measurement accuracy even in cases where vibrations, variations in the flow rate and pressure, or the like occurs.

According to one or more aspects of the present invention, the measuring device can be used under high pressure and can measure impurity particles contained in a hydraulic oil with high accuracy.

DESCRIPTION OF EMBODIMENTS

Embodiments of the present invention will be described in detail below with reference to the drawings. A pollution level measurement device 1 is provided in an apparatus 100, such as construction machinery and a hydraulic device, that uses a hydraulic oil to perform a desired operation.

Figure 1:
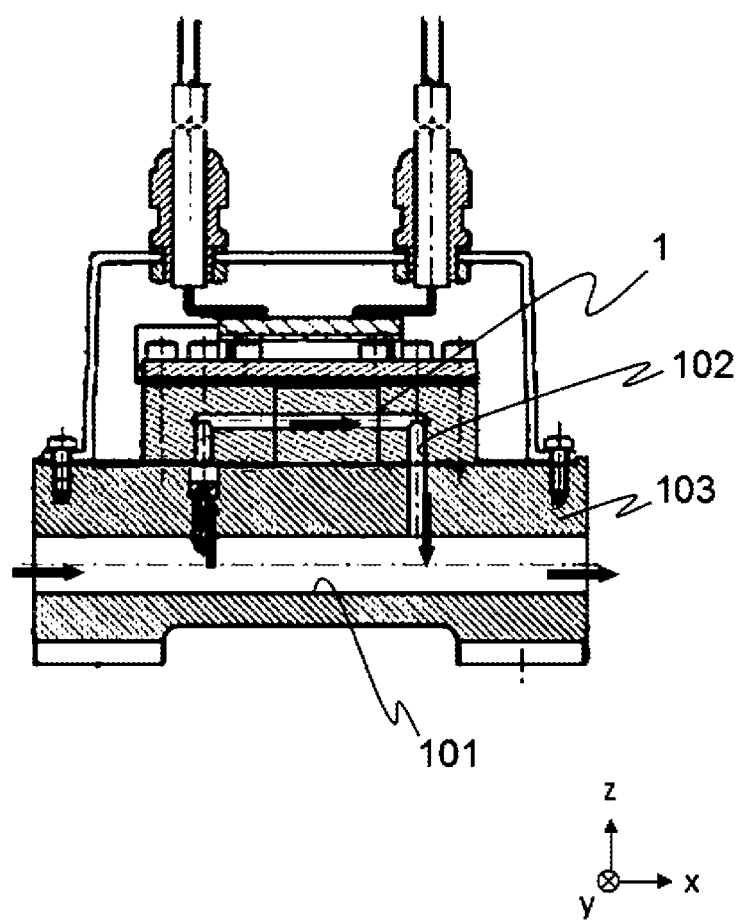
FIG. 1 illustrates an overview of an apparatus 100 provided with a pollution level measurement device 1 according to an example of the present invention.

FIG. 1 illustrates an overview of the apparatus 100. The apparatus 100 includes a housing 103 provided with a main flow path 101 and a bypass flow path 102 in which a hydraulic oil to be measured flows. The pollution level measurement device 1 is disposed in such a desired position in the apparatus 100 as to include the bypass flow path 102.

The thick arrows in FIG. 1 indicate a flow of the hydraulic oil in the apparatus 100. The hydraulic oil flows from a −x direction toward a +x direction in the main flow path 101. The hydraulic oil flowing in the main flow path 101 partially flows into the bypass flow path 102 and is supplied to the pollution level measurement device 1. The hydraulic oil flowing out from the pollution level measurement device 1 passes through the bypass flow path 102 and returns to the main flow path 101.

Figure 2:
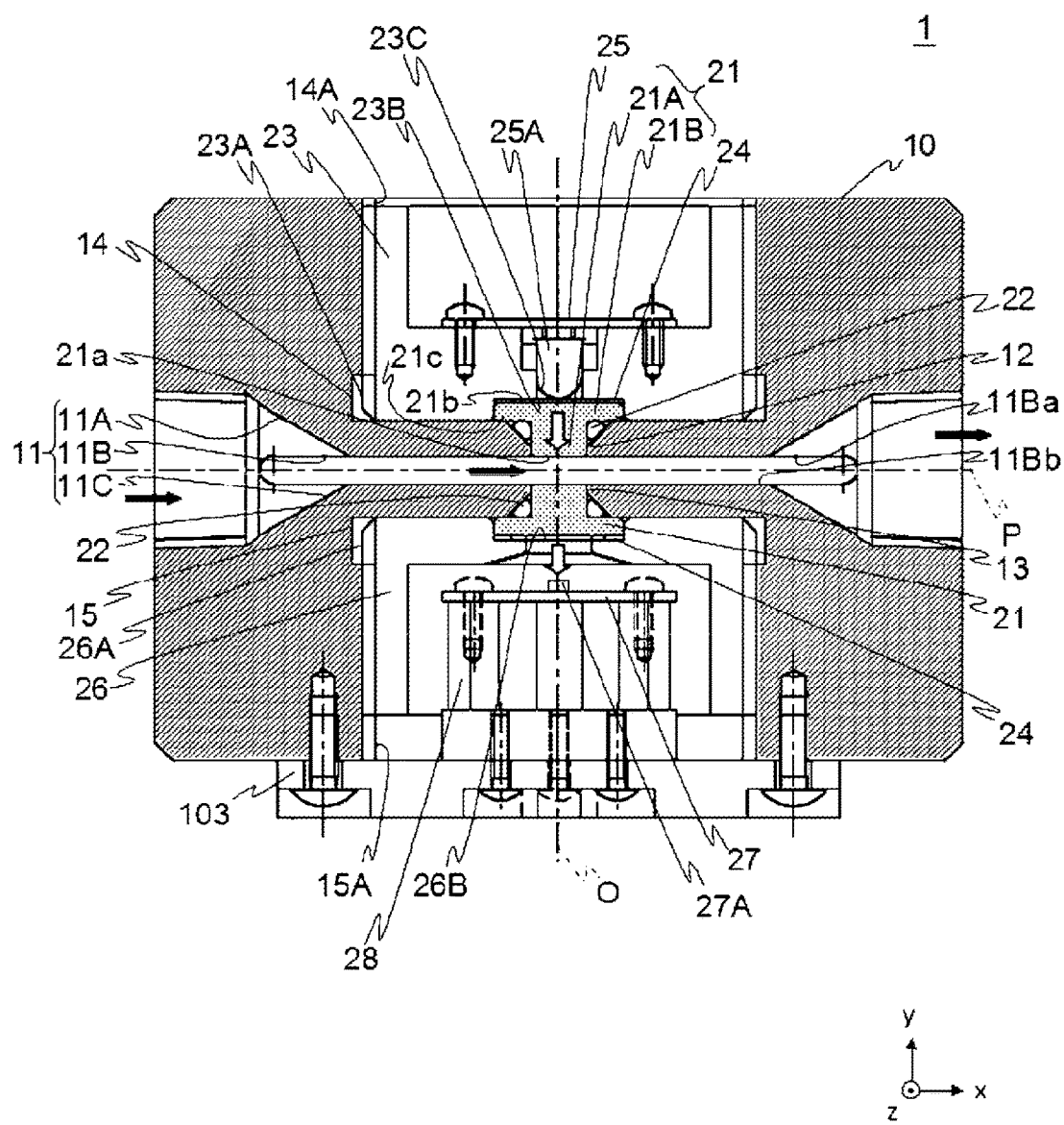
FIG. 2 is a cross-sectional view illustrating an overview of the pollution level measurement device 1.

FIG. 2 is a cross-sectional view illustrating an overview of the pollution level measurement device 1. The pollution level measurement device 1 mainly includes a housing 10, glass cells 21, O-rings 22, a plug 23, packings 24, a light emitting section substrate 25, a plug 26, a light receiving section substrate 27, and a block 28. Note that, in FIG. 3, the hatching indicating a cross section is partially omitted.

The housing 10 is a substantially rectangular member made from metal (such as iron and aluminum), for example. The housing 10 has a body 10A (see FIGS. 3 to 6) mainly provided with a measurement flow path 11 through which the hydraulic oil to be measured flows, holes 12, 13 serving as windows for guiding light into and out of the measurement flow path 11, a cavity 14 into which the plug 23 is attached, and a cavity 15 into which the plug 26 is attached.

The measurement flow path 11 has openings in a side surface on a −x side and a side surface on a +x side of the body 10A. A center axis P of the measurement flow path 11 is orthogonal to the side surface on the −x side and the side surface on the +x side. The measurement flow path 11 has a side surface Ba and a side surface Bb that are flat surfaces parallel with the center axis P.

The holes 12, 13 are formed facing each other across the center axis P. One end of each of the holes 12, 13 opens to the measurement flow path 11. The hole 12 communicates with the cavity 14, and the hole 13 communicates with the cavity 15. The centers of the holes 12, 13 and the cavities 14, 15 are substantially orthogonal to the center axis P.

Note that the shape of the housing 10 is not limited to a substantially rectangular shape. The housing 10 may have any shape that has two facing surfaces on which the measurement flow path 11 opens. The housing 10 will be described in detail later.

The glass cells 21 are substantially cylindrical members made from an optically transparent material (such as glass). The glass cells 21 each include a main portion 21A having a substantially cylindrical shape and a flange portion 21B having a substantially thick circular plate shape with a diameter greater than a diameter of the main portion 21A. The glass cells 21 are disposed in the holes 12, 13. Since the holes 12, 13 open to the measurement flow path 11, end surfaces 21a of the glass cells 21 disposed in the holes 12, 13 directly come into contact with the hydraulic oil flowing in the measurement flow path 11. The end surfaces 21a of the glass cells 21 disposed in the holes 12, 13 and the side surfaces 11Ba, 11Bb of the measurement flow path 11 are substantially in the same plane.

Since the end surfaces 21a of the glass cells 21 and the side surfaces 11Ba, 11Bb are substantially in the same plane, swirls can be prevented from being generated in the hydraulic oil flowing in the measurement flow path 11 around the glass cells 21.

The O-rings 22 are annular packings having a substantially circular cross section, for example. When the glass cells 21 are disposed in the holes 12, 13, the O-rings 22 are disposed between the holes 12, 13 and the glass cells 21. The O-rings 22 function as sealing members that elastically deform between the holes 12, 13 and the glass cells 21 to prevent the hydraulic oil from leaking from between the holes 12, 13 and the glass cells 21.

The plug 23 is a substantially cylindrical member made from metal (such as aluminum). A screw 23A is formed on the outer periphery of the plug 23. By engaging the screw 23A with a screw 14A formed on the inner periphery of the cavity 14, the plug 23 is attached to the housing 10.

The plug 23 has a recess 23B formed having substantially the same diameter as a diameter of the flange portion 21B. The flange portion 21B fits in the recess 23B.

The packings 24 are substantially cylindrical plate shaped members made from metal (such as brass). A packing 24 is disposed between the recess 23B and the flange portion 21B. When the screw 23A is engaged with the screw 14A to attach the plug 23 to the housing 10, the plug 23 presses an end surface 21b of the flange portion 21B via the packing 24. As a result, an end surface 21c, on the main portion 21A side, of the flange portion 21B is pressed against the body 10A. The contact surface between the end surface 21c and the body 10A has a substantially circular plate shape, such that the glass cell 21 is supported on the surface. This configuration allows the glass cell 21 to be securely fixed to the hole 12.

Note that, e.g., as an alternative embodiment, the plug 23 may be applied without the packing 24 to press the flange portion 21B directly.

The light emitting section substrate 25 is provided with a light emitting section (for example, an LED) 25A emitting light. Light emitted from the light emitting section 25A passes through the glass cell 21 disposed in the hole 12 and irradiates the hydraulic oil flowing in the measurement flow path 11.

The light emitting section substrate 25 is attached to the plug 23 with screws. The light emitting section 25A is inserted into a hole 23C formed in the plug 23, such that an optical axis O being the center of the light emitted from the light emitting section 25A is positioned substantially coinciding with the center axes of the holes 12, 13. The light emitting section 25A is disposed adjacent to the flange portion 21B.

The light emitted from the light emitting section 25A enters the glass cell 21 from a direction orthogonal to the flat end surface 21a of the glass cell 21. Thus, the light emitted from the light emitting section 25A passes through the glass cell 21 along the center axis (substantially coinciding with the optical axis O) of the glass cell 21, without diffusing on the end surface 21a. The end surface 21b of the glass cell 21 is also flat, such that light passing through the glass cell 21 exits in a direction orthogonal to the end surface 21b. Thus, the light emitted from the light emitting section 25A irradiates the hydraulic oil in the measurement flow path 11 without diffusing.

Similar to the plug 23, the plug 26 is a substantially cylindrical member made from metal (such as aluminum). A screw 26A is formed on the outer periphery of the plug 26. By engaging the screw 26A with a screw 15A formed on the inner periphery of the cavity 15, the plug 26 is attached to the housing 10.

The plug 26 has a recess 26B formed having substantially the same diameter as the diameter of the flange portion 21B. The flange portion 21B fits in the recess 26B.

When the screw 26A is engaged with the screw 15A to attach the plug 26 to the housing 10, the plug 26 presses the flange portion 21B via the packing 24. As a result, the end surface 21c of the flange portion 21B is pressed against the body 10A. This configuration allows the glass cell 21 to be fixed to the hole 13. Note that the positional relationship between the hole 13 and the glass cell 21 and the method of attaching the glass cell 21 to the hole 13 are the same as the positional relationship between the hole 12 and the glass cell 21 and the method of attaching the glass cell 21 to the hole 12.

The light receiving section substrate 27 is provided with a light receiving element 27A detecting light transmitted resulting from the light emission. The light receiving element 27A is, for example, a photodiode (PD) and is disposed facing the light emitting section 25A across the measurement flow path 11 and the glass cells 21. The light receiving element 27A is disposed on the optical axis O.

Light emitted from the light emitting section 25A and not reflected by impurity particles contained in the hydraulic oil in the measurement flow path 11 enters the glass cell 21 from a direction orthogonal to the end surface 21b. Light passing through the glass cell 21 exits in a direction orthogonal to the end surface 21a. Thus, most of the light emitted from the light emitting section 25A and not reflected by impurity particles contained in the hydraulic oil in the measurement flow path 11 (light that passed through the hydraulic oil) is received by the light receiving element 27A.

The light receiving section substrate 27 is attached to the block 28 with screws. The block 28 is fixed to the housing 10 by screwing or the like. Note that no such limitation is intended for attaching the light receiving section substrate 27, and the light receiving section substrate 27 may be fixed to the plug 26 by screwing, for example.

Figure 3:
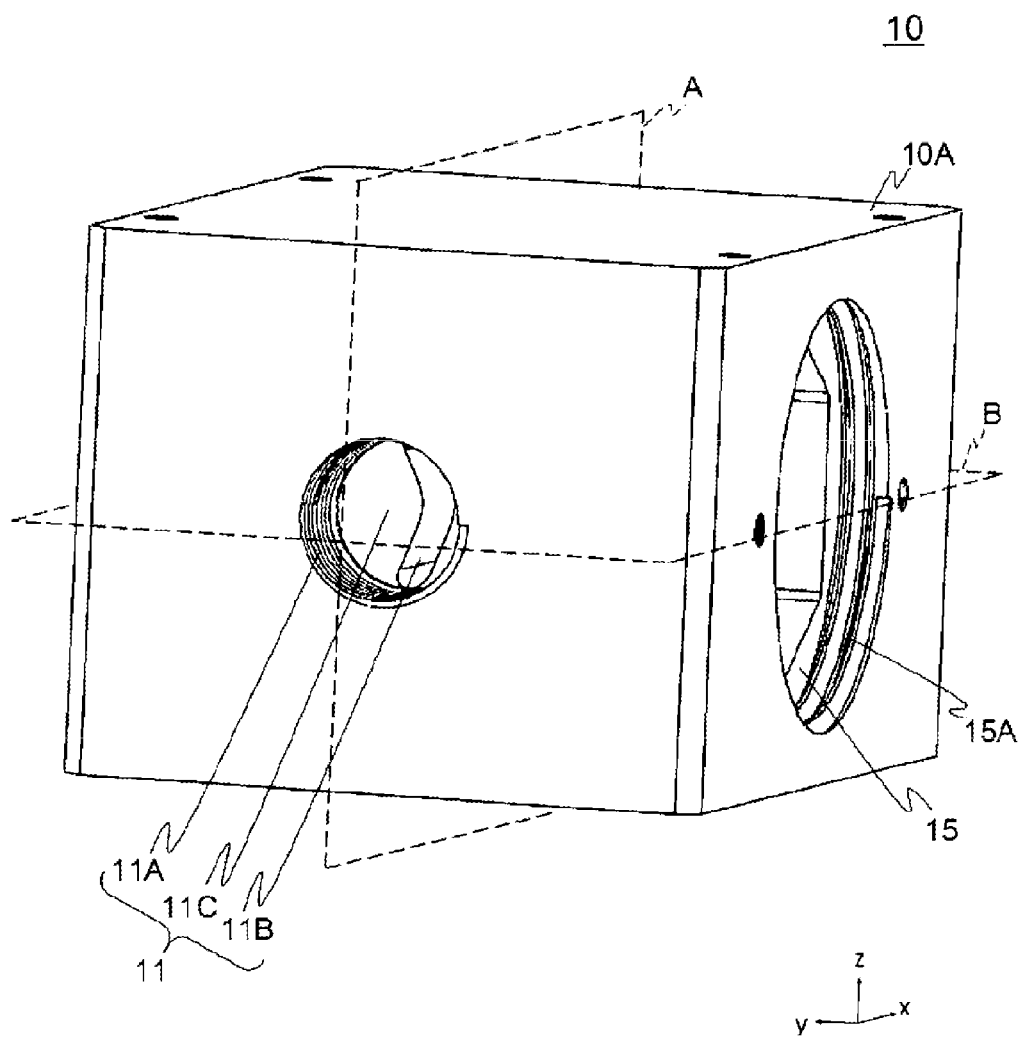
FIG. 3 is a perspective view of a housing 10.

Next, the housing 10 will be described in detail. FIG. 3 is a perspective view of the housing 10. The measurement flow path 11 extending from the −x side surface to the +x side surface of the body 10A is formed in the body 10A. The cavity 14 is formed in a +y side surface of the body 10A, and the cavity 15 is formed on a −y side surface of the body 10A. The measurement flow path 11 will be described in detail below.

Figure 4:
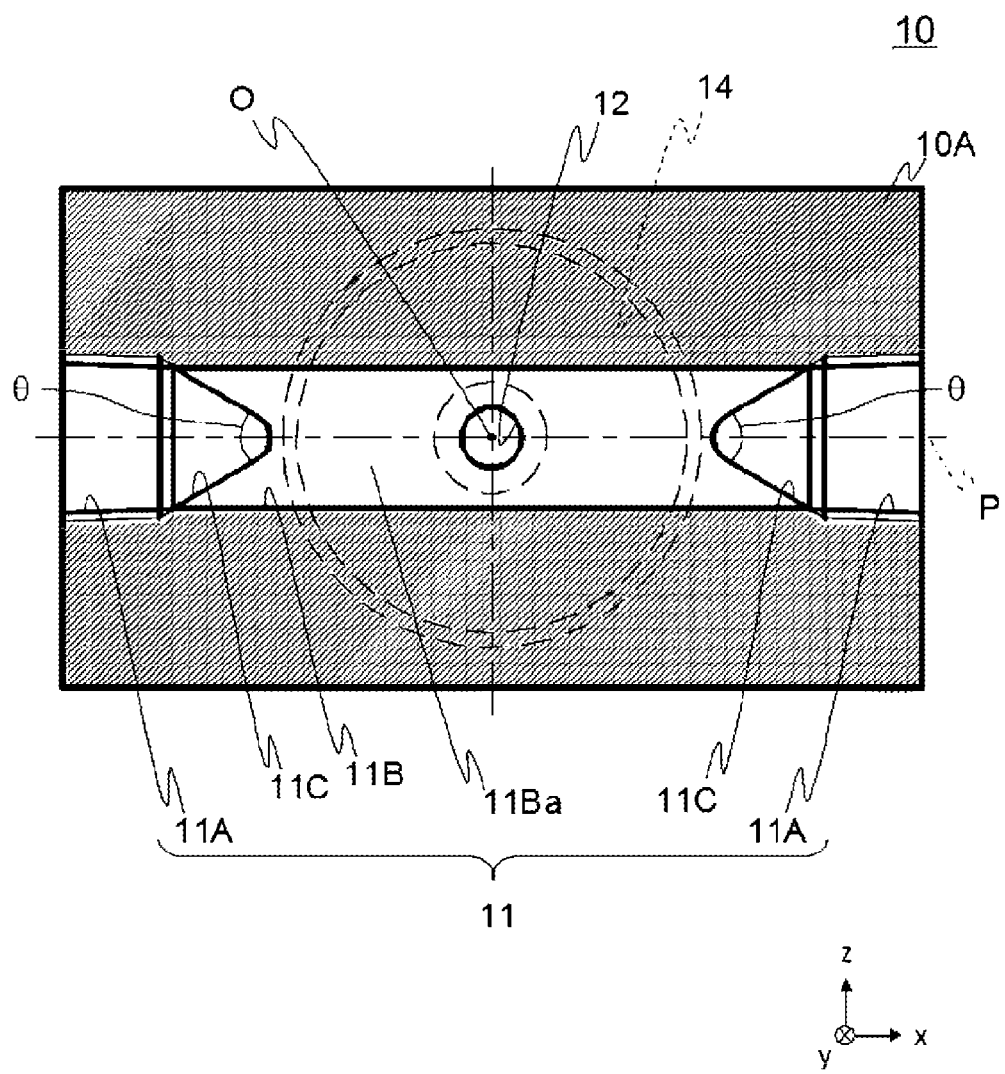
FIG. 4 is a cross-sectional view of the housing 10 in plane A in FIG. 3.
Figure 5:
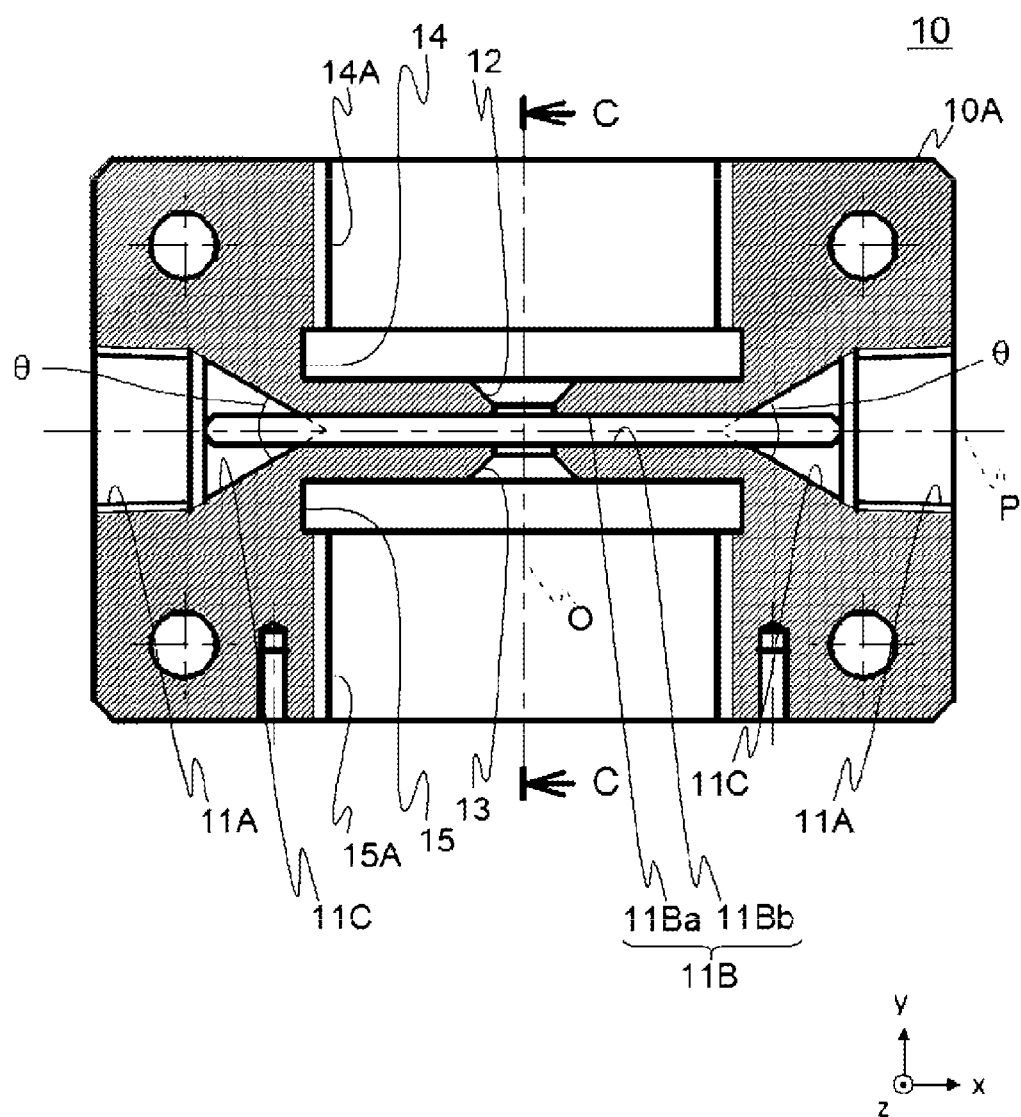
FIG. 5 is a cross-sectional view of the housing 10 in plane B in FIG. 3.
Figure 6:
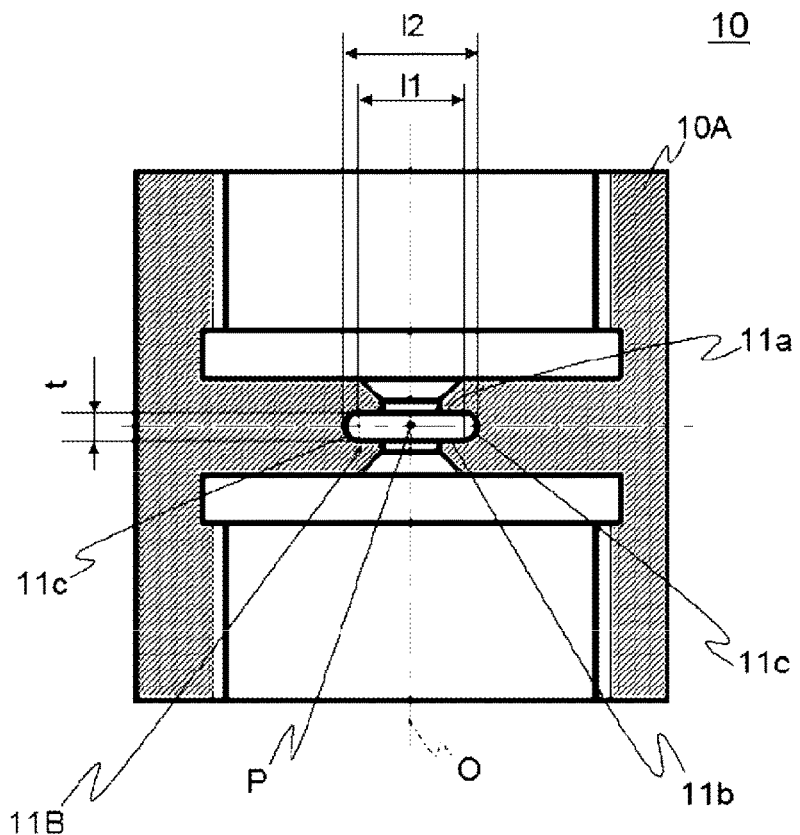
FIG. 6 is a cross-sectional view taken along line C-C in FIG. 5.

FIG. 4 is a cross-sectional view of the housing 10 in plane A in FIG. 3. FIG. 5 is a cross-sectional view of the housing 10 in plane B in FIG. 3. FIG. 6 is a cross-sectional view taken along line C-C in FIG. 5.

The measurement flow path 11 includes substantially cylindrical screw portions 11A formed on both sides of the measurement flow path 11, a long cavity portion 11B having a cross section shaped into a long cavity when cut in a plane substantially parallel with an yz plane, and linking portions 11C gradually linking the screw portions 11A with the long cavity portion 11B.

The screw portions 11A are each coupled with another component, for example, a joint that includes a flow path having a substantially circular cross section. The screw portion 11A disposed on the −x side serves as an inflow section allowing the hydraulic oil to flow into the measurement flow path 11, and the screw portion 11A disposed on the +x side serves as an outflow section allowing the hydraulic oil to flow out from the measurement flow path 11.

The long cavity portion 11B has the side surfaces 11Ba, 11Bb. The side surfaces 11Ba, 11Bb are flat surfaces with their longitudinal direction substantially parallel with the x direction (see FIG. 4) and face each other across the center axis P (see FIGS. 5 and 6). One end of the hole 12 opens on the side surface 11Ba, and one end of the hole 13 opens on the side surface 11Bb (the hole 13 is not illustrated in FIG. 4).

As illustrated in FIG. 6, the shape of the cross section in a plane substantially orthogonal to the center axis P of the measurement flow path 11 (hereinafter referred to as "cross-sectional shape") of the long cavity portion 11B is a long cavity. The long cavity portion 11B has two linear sides 11a, 11b extending in a direction (z direction) substantially orthogonal to the optical axis O and curved sides 11c connecting the sides 11a, 11b, in the plane substantially orthogonal to the center axis P. The side 11a composes part of the side surface 11Ba, and the side 11b composes part of the side surface 11Bb.

In the present embodiment, the sides 11a, 11b have a length 11 of approximately 11 mm, and the long cavity portion 11B has a width 12 of approximately 14 mm and a thickness (distance between the side 11a and the side 11b) t of approximately 3 mm. In this way, the thickness t of the long cavity portion 11B is sufficiently smaller than the length 11 of the sides 11a, 11b (the length of the side surfaces 11Ba, 11Bb in a direction substantially orthogonal to the center axis P) and the width 12 of the long cavity portion 11B.

The linking portions 11C have such a tapered shape that the cross-sectional shape of the flow path gradually changes from a round cavity being the cross-sectional shape of the screw portions 11A to the long cavity being the cross-sectional shape of the long cavity portion 11B.

The linking portions 11C have a substantially truncated cone shape. As illustrated in FIG. 4, the holes connecting the linking portions 11C with the long cavity portion 11B in plane A have a substantially triangular shape protruding toward the center of the housing 10.

The width 12 of the long cavity portion 11B is substantially the same as the diameter of the screw portion 11A. Note that the diameter of the screw portion 11A is only required to be greater than or equal to the width 12 of the long cavity portion 11B and is not limited to being substantially the same as the width 12 of the long cavity portion 11B.

The linking portions 11C are each formed such that an angle θ formed by two lines facing across the center axis P is approximately 60 degrees in plane A and plane B that contain the center axis P. The angle θ will be described in detail later.

The action of the pollution level measurement device 1 thus configured will be described with reference to FIG. 2. In FIG. 2, the solid arrows indicate the flow of the hydraulic oil, and the hollow arrows indicate a path of the light.

The hydraulic oil flows into the pollution level measurement device 1 from the inflow section being the screw portion 11A formed on the −x side of the housing 10. The hydraulic oil introduced from the inflow section passes through the linking portion 11C and flows into the long cavity portion 11B.

The hydraulic oil introduced into the long cavity portion 11B flows downstream in the long cavity portion 11B (in the direction from −x toward +x) and flows out of the pollution level measurement device 1 from the outflow section being the screw portion 11A formed on the +x side of the housing 10.

The hydraulic oil flowing downstream in the long cavity portion 11B is irradiated with light from the light emitting section 25A. The light emitted from the light emitting section 25A enters the glass cell 21 from the end surface 21b, passes through the glass cell 21, and is incident on the hydraulic oil in the measurement flow path 11 from the end surface 21a. The light passing through the measurement flow path 11 enters the glass cell 21 from the end surface 21a, passes through the glass cell 21, and exits from the end surface 21b. The light receiving element 27A receives the light exiting from the end surface 21b.

In the present embodiment, the light emitting section 25A continuously emits light. The light receiving element 27A continuously receives light. An output signal from the light receiving element 27A is amplified by an amplifier. The amount of impurity particles contained in the hydraulic oil flowing in the measurement flow path 11 is measured on the basis of the amplified signal. The description of a method of measuring the amount of impurity particles is omitted because various techniques are already known. The output signal from the light receiving element 27A may be processed by an electric circuit or a microcomputer (not illustrated) provided in the pollution level measurement device 1 or by a device other than the pollution level measurement device 1.

The light receiving element 27A continuously receives light. Thus, in a case where the flow of the hydraulic oil flowing in the measurement flow path 11 is disturbed, the measurement accuracy decreases. Use of the linking portions 11C having the angle θ of approximately 60 degrees in the present embodiment stabilizes the flow of the hydraulic oil and can thus increase the measurement accuracy. This point will be described in detail below.

Figure 7:
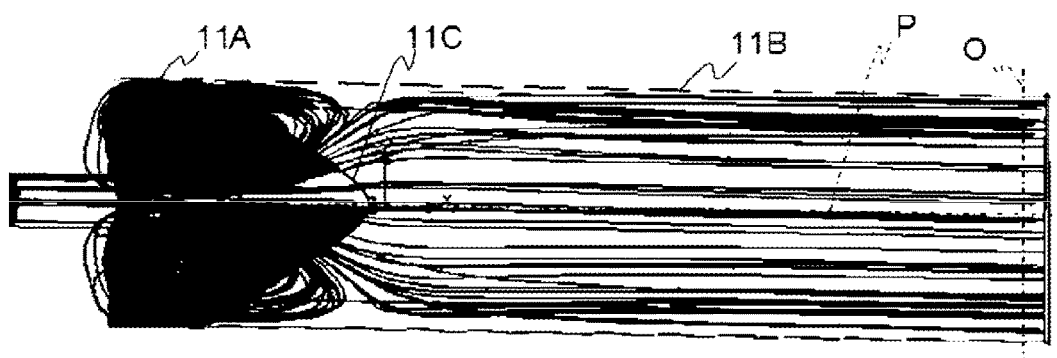
FIG. 7 is a schematic view illustrating a flow of a hydraulic oil in the case of a linking portion 11C having an angle θ of approximately 60 degrees (in an embodiment).
Figure 8:
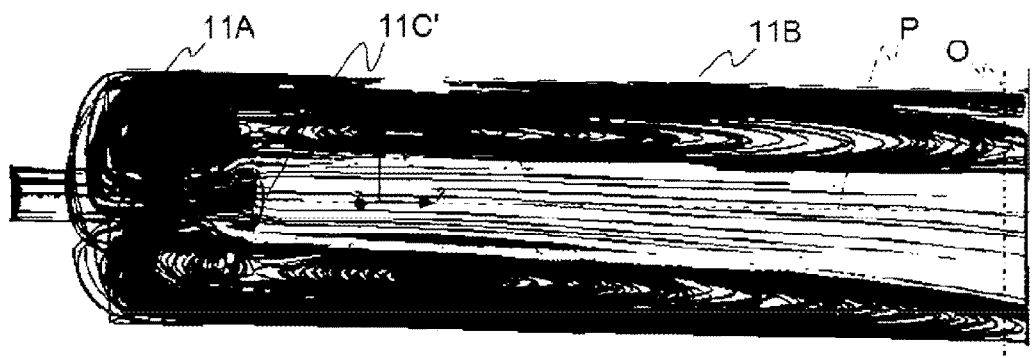
FIG. 8 is a schematic view illustrating a flow of a hydraulic oil in the case of a linking portion 11C having an angle θ of approximately 120 degrees (in Comparative Example).
Figure 9:
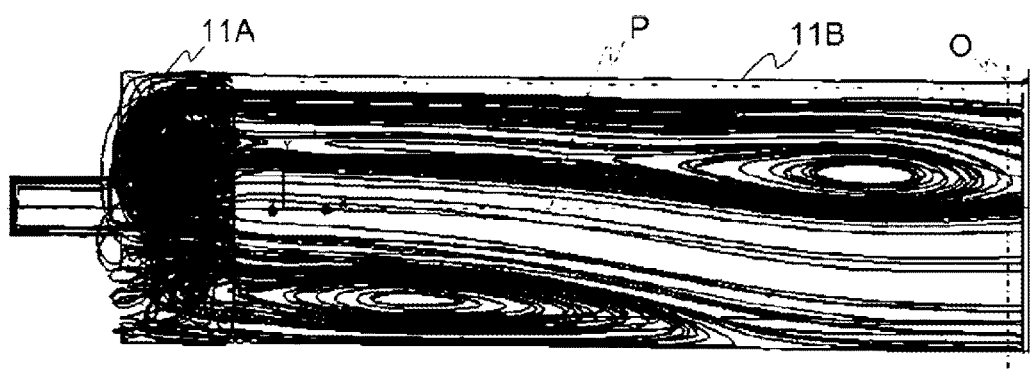
FIG. 9 is a schematic view illustrating a flow of a hydraulic oil in the case of no linking portion is provided (in Comparative Example).

FIG. 7 is a schematic view illustrating a flow of the hydraulic oil in a case of the linking portion 11C having the angle θ of approximately 60 degrees (in the present embodiment). FIG. 8 is a schematic view illustrating a flow of the hydraulic oil in a case of a linking portion 11C' having the angle θ of approximately 120 degrees (in Comparative Example). FIG. 9 is a schematic view illustrating the flow of the hydraulic oil in a case of no linking portion is provided (in Comparative Example). Only the linking portion is different among FIGS. 7 to 9. The lines illustrated in FIGS. 7 to 9 indicate path lines in simulations of the flow of the hydraulic oil.

Note that, although a pipe thinner than the screw portion 11A is provided on the left side of the measurement flow path 11 via the screw portion 11A in FIGS. 7 to 9, the pipe is not limited to having such a diameter.

As illustrated in FIG. 7, in the case of the angle θ is approximately 60 degrees, swirls are generated around the linking portion 11C, whereas no swirl is generated in the vicinity of the optical axis O. On the other hand, as illustrated in FIG. 8, in the case of the angle θ is approximately 120 degrees, swirls are continuously generated around the linking portion 11C toward the downstream side in the vicinities of both ends of the long cavity portion 11B. In the case illustrated in FIG. 9, swirls are generated even at the center portion of the long cavity portion 11B (in the vicinity of the center axis P).

A swirl disturbs movement of impurity particles contained in the hydraulic oil. This disturbance may cause multiple measurements of the same impurity particle. It is thus desirable to minimize generation of swirls to increase the measurement accuracy.

In the case illustrated in FIG. 8, swirls are generated only in the vicinities of both ends of the long cavity portion 11B. Thus, by making an even longer flow path, swirls can be minimized to such an extent that a measurement error can be ignored. However, in the case where no linking portion is provided as illustrated in FIG. 9, swirls remain generated even with a longer flow path, and impurity particles cannot be measured.

Thus, the linking portions 11C, 11C' having such a tapered shape that the cross-sectional shape of the flow path gradually changes are required to be disposed between the screw portions 11A and the long cavity portion 11B. To prevent a swirl from being generated in a position other than the linking portions, the angle θ of the tapered shape is desirable to be approximately 60 degrees.

According to the present embodiment, the measurement flow path 11 is formed directly in the housing 10, such that the pollution level measurement device 1 can be used under high pressure. In a case where the measurement flow path is formed with a glass tube, for example, an increase in pressure of a hydraulic oil or the like flowing in the pipe may generate a crack or the like in the measurement flow path. In contrast, by forming a hole serving as the measurement flow path 11 in the housing 10, generation of a crack or the like in the measurement flow path 11 can be prevented even under high pressure.

In the present embodiment, the substantially cylindrical glass cells 21 are used as windows for guiding light into and out of the measurement flow path 11, such that the pollution level measurement device 1 can be used under high pressure. In the case where the measurement flow path is formed with a glass tube, for example, the glass tube exhibits low pressure resistance due to its curved surface. In contrast, the glass cells 21 have the flat end surfaces and are thick and rigid. Thus, generation of a crack or the like in the glass cells 21 can be prevented even under high pressure.

In the present embodiment, no curved surface is present on an optical path from the light emitting section 25A to the light receiving element 27A, such that impurity particles contained in the hydraulic oil can be measured with high accuracy. In the case where the measurement flow path is formed with a glass tube, for example, light is refracted in varies directions by the surface of the glass tube because of the curved surface of the glass tube. In contrast, light emitted from the light emitting section 25A enters or exits in the direction orthogonal to the flat end surfaces of the glass cells 21. Thus, the light emitted from the light emitting section 25A irradiates the hydraulic oil in the measurement flow path 11 as it is without diffusing. Accordingly, the measurement accuracy can be increased.

In the present embodiment, the long cavity portion 11B has a small thickness, such that the optical path, that is, the distance between the light emitting section 25A and the light receiving element 27A, is shortened, resulting in an increase in the measurement accuracy.

According to the present embodiment, the linking portions 11C having such a tapered shape that the cross-sectional shape of the measurement flow path 11 changes from a round cavity to a long cavity stabilize the flow of the hydraulic oil, resulting in an increase in the measurement accuracy.

According to the present embodiment, the end surfaces 21a of the glass cells 21 and the side surfaces 11Ba, 11Bb of the measurement flow path 11 are substantially in the same plane, such that swirls are prevented from being generated in the hydraulic oil flowing in the measurement flow path 11 around the glass cells 21, resulting in an increase in the measurement accuracy. In a case where the glass cells 21 protrude in the measurement flow path 11, for example, the hydraulic oil flowing in the measurement flow path 11 collides against the glass cells 21 and thus generating swirls. In contrast, in a case where the end surfaces 21a and the side surfaces 11Ba, 11Bb are substantially in the same plane, the glass cells 21 do not disturb the flow of the hydraulic oil, resulting in prevention of swirls from being generated around the glass cells 21, that is, in the vicinity of the optical axis O. Accordingly, the measurement accuracy can be increased.

According to the present embodiment, when the glass cells 21 are attached to the housing 10, the end surfaces 21c of the flange portions 21B come into contact with the housing 10, resulting in an improvement in vibration resistance. In the case where the measurement flow path is formed with a glass tube, for example, vibration of the pollution level measurement device 1 may cause the glass tube to vibrate more vigorously than the pollution level measurement device 1 because periphery of the glass tube is fixed. In contrast, in a case where the glass cells 21 and the housing 10 come into surface contact with each other, the glass cells 21 can be pressed against the housing 10 with strong force. Thus, even in the case where the pollution level measurement device 1 vibrates, the glass cells 21 are less likely to vibrate with the pollution level measurement device 1 (improve in vibration resistance). Furthermore, since the glass cells 21 and the housing 10 come into surface contact with each other, variations in the flow rate or pressure of the hydraulic oil flowing in the measurement flow path 11 are less likely to cause vibration of the glass cells 21. Accordingly, the measurement accuracy can be improved.

Note that in the present embodiment, the thickness t of the long cavity portion 11B (approximately 3 mm) is sufficiently smaller than the length l1 of the sides 11a, 11b (approximately 11 mm) and the width l2 of the long cavity portion 11B (approximately 14 mm) in the plane substantially orthogonal to the center axis P of the measurement flow path 11; however, the cross-sectional shape of the long cavity portion 11B is not limited to this configuration. For example, the long cavity portion 11B may have a thickness t of greater than approximately 3 mm. However, in order to increase the measurement accuracy, it is desirable to minimize the thickness t of the long cavity portion 11B to shorten the optical path.

In the present embodiment, the cross-sectional shape of the long cavity portion 11B is a long cavity having the two linear sides 11a, 11b extending in the direction (z direction) substantially orthogonal to the optical axis O but the cross-sectional shape of the long cavity portion 11B is not limited to this configuration. For example, the cross-sectional shape of the long cavity portion may be substantially rectangular. However, in order to shorten the optical path, it is desirable that the length of the long cavity portion in the y direction (direction parallel with the optical axis O) is shorter than the length of the long cavity portion in the z direction.

Alternatively, the cross-sectional shape of the long cavity portion may be substantially oval, for example. In this case, the minor axis of the substantially oval shape may be substantially parallel with the y direction, the major axis may be substantially parallel with the z direction, and a portion on the +y side and a portion on the −y side may be side surfaces of the long cavity portion. These side surfaces of the long cavity portion are curved, and the glass cells 21 thus partially protrude from the side surfaces of the long cavity portion. However, the amount of the protrusions of the glass cells 21 is small depending on the oval shape, such that even in a case where a swirl is generated, the swirl does not affect the measurement accuracy. In order to prevent generation of swirls, it is desirable that the cross-sectional shape of the long cavity portion is a long cavity.

In the present embodiment, the measurement flow path 11 includes the screw portions 11A, the long cavity portion 11B, and the linking portions 11C; however, the measurement flow path 11 is not limited to having this shape. For example, in a case where the cross-sectional shape of the bypass flow path 102 is a long cavity, the measurement flow path may include only the long cavity portion 11B. However, in a case where the cross-sectional shape of the bypass flow path 102 is a round hole, it is desirable that the linking portions 11C are formed on both ends of the long cavity portion 11B.

Second Embodiment

In the first embodiment of the present invention, the measurement flow path 11 includes the screw portions 11A, the long cavity portion 11B, and the linking portions 11C, and the diameter of the round cavities of the screw portions 11A (on both ends of the measurement flow path 11) is substantially equal to the width of the long cavity portion 11B. However, the measurement flow path 11 is not limited to having this shape.

In the first embodiment of the present invention, the diameter of the round cavities on both ends of the measurement flow path 11 is smaller than the width of the long cavity portion 11B. A pollution level measurement device 2 according to a second embodiment will be described below. Note that the same components as those in the first embodiment are denoted using the same reference signs, and descriptions thereof will be omitted.

The pollution level measurement device 2 mainly includes a housing 10-1, the glass cells 21, the O-rings 22, the plug 23, the packings 24, the light emitting section substrate 25, the plug 26, the light receiving section substrate 27, and the block 28.

Figure 10:
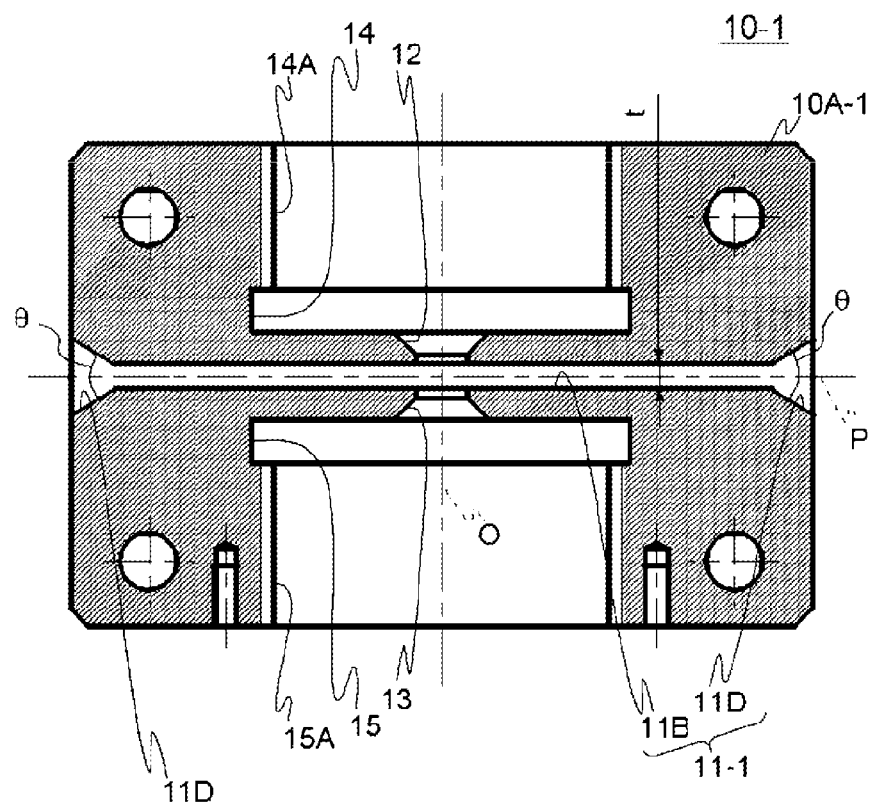
FIG. 10 is a cross-sectional view illustrating an overview of a housing 10-1.

FIG. 10 is a cross-sectional view illustrating an overview of the housing 10-1. The housing 10-1 is a substantially rectangular member made from metal (such as aluminum). The housing 10-1 has a body 10A-1 mainly provided with a measurement flow path 11-1, the holes 12, 13, the cavity 14, and the cavity 15.

The measurement flow path 11-1 mainly includes the long cavity portion 11B and guiding portions 11D disposed on both ends of the long cavity portion 11B.

The guiding portions 11D each have one end communicating with the long cavity portion 11B and the other end opening on an end surface of the housing 10-1. The opening formed on the end surface of the housing 10-1 has a substantially circular shape. The guiding portions 11D have such a tapered shape that the cross-sectional shape of the flow path gradually changes from a round cavity to the long cavity being the cross-sectional shape of the long cavity portion 11B. The guiding portion 11D disposed on the −x side serves as an inflow section allowing the hydraulic oil to flow into the measurement flow path 11-1, and the guiding portion 11D disposed on the +x side serves as an outflow section allowing the hydraulic oil to flow out from the measurement flow path 11-1.

Figure 11:
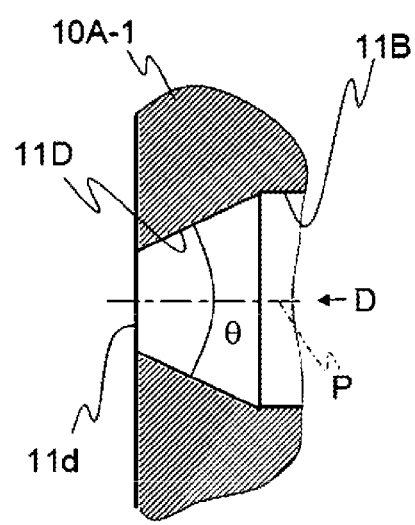
FIG. 11 illustrates a shape of a guiding portion 11D.
Figure 12:
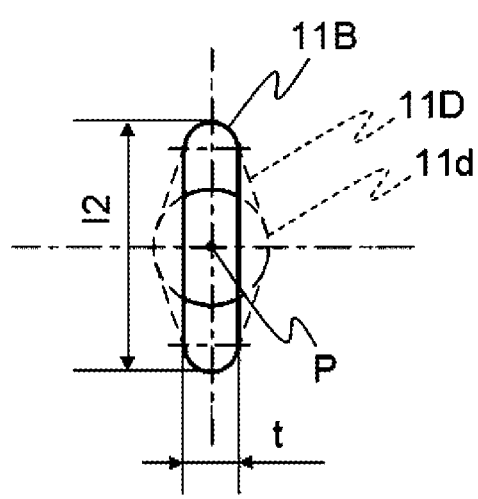
FIG. 12 is a view taken along line D in FIG. 11.

FIGS. 11 and 12 illustrate a shape of the guiding portion 11D. FIG. 11 is a cross-sectional view, and FIG. 12 is a view taken a long line D in FIG. 11. The body 10A-1 is omitted in FIG. 12.

The opening 11d formed on the end surface of the housing 10-1 is a round cavity having a diameter smaller than the width 12 of the long cavity portion 11B and greater than the thickness t of the long cavity portion 11B. Similar to the first embodiment, an angle θ formed by two lines facing across the center axis P of the guiding portion 11D is approximately 60 degrees.

According to the present embodiment, the circular pipe is gradually changed to the long cavity, such that swirls are not being generated in the hydraulic oil flowing in the measurement flow path 11-1, resulting in a stable flow. Accordingly, impurity particles contained in the hydraulic oil can be measured with high accuracy. For example, in the first embodiment, the cross-sectional area of the measurement flow path 11 becomes smaller, such that swirls are generated in the vicinities of the linking portions 11C. In contrast, in the present embodiment, the cross-sectional shape is changed gradually from a circle to the long cavity without a significant change in the cross-sectional area of the measurement flow path 11-1. Thus, the flow of the hydraulic oil is further stabilized, resulting in prevention of generation of swirls.

Embodiments of the invention have been described in detail with reference to the drawings; however, specific configurations are not limited to the embodiments, and changes in the design or the like are also included within a scope which does not depart from the gist of the invention. For example, the above examples have been explained in detail in order to facilitate understanding of the present invention and are not necessarily limited to examples provided with the entirety of the configuration described above. In addition, a part of the configuration of an embodiment may be replaced with the configuration of another embodiment and the configuration of another embodiment may be added to, deleted from, or replaced with the configuration of an embodiment.

Further, in the present invention, "substantially/approximately" is a concept that includes variation or modification to the extent that sameness is not lost, and does not only mean strictly the same. For example, "substantially orthogonal" is not limited to being strictly orthogonal, and is a concept that includes an error of several degrees, for example. Further, simple expressions such as orthogonal, parallel, and matching are not to be understood as merely being strictly orthogonal, parallel, matching, and the like, and include being substantially parallel, substantially orthogonal, substantially matching, and the like.

Furthermore, the meaning of the term "in the vicinity" in the present invention includes a region of a range (which can be determined as desired) near a position serving as a reference. For example, "in the vicinity of the end" refers to a region of a range near the end, and is a concept indicating that the end may or may not be included.

REFERENCE SIGNS LIST 1, 2 Pollution level measurement device
10, 10-1 Housing
10A, 10A-1 Body
11, 11-1 Measurement flow path
11A Screw portion
11B Long cavity portion
11Ba, 11Bb Side surface
11C Linking portion
11C' Linking portion
11D Guiding portion
11a, 11b Side
11c Side
11d Opening
12, 13 Hole
14 Cavity
14A Screw
15 Cavity
15A Screw
21 Glass cell
21A Main portion
21B Flange portion
21a, 21b End surface
22 O-ring
23 Plug
23A Screw
23B Recess
23C Hole
24 Packing
25 Light emitting section substrate
25A Light emitting section
26 Plug
26A Screw
26B Recess
27 Light receiving section substrate
27A Light receiving element
28 Block
100 Apparatus
101 Main flow path
102 Bypass flow path
103 Housing

The invention claimed is:
1. A measuring device comprising:
a housing comprising two surfaces facing away from each other, the housing being provided with a flow path structure, a first cavity, and a second cavity, wherein
the flow path structure has two openings on the two surfaces respectively and comprises a first side surface and a second side surface facing each other,
the first cavity comprises one end opening on the first side surface,
the second cavity faces the first cavity across a center axis of the flow path structure and comprises one end opening on the second side surface;
a first cell disposed in the first cavity, made from a transparent material, and having a substantially cylindrical shape, both end surfaces of the first cell being flat surfaces;
a second cell disposed in the second cavity, made from a transparent material, and having a substantially cylindrical shape, both end surfaces of the second cell being flat surfaces;
a light emitting section configured to irradiate a hydraulic oil flowing in the flow path structure with light via the first cell in a direction substantially orthogonal to the center axis; and
a light receiving section disposed facing the light irradiating section across the first cell, the flow path structure, and the second cell;
the first cavity and the second cavity having centers substantially coinciding with an optical axis being a center of light emitted from the light irradiating section, wherein:
the flow path structure comprises both ends shaped into a round cavity;
the flow path structure has such a tapered shape that a shape in a plane substantially orthogonal to the center axis changes from the round cavity to a long cavity having two sides substantially orthogonal to the optical axis; and
the tapered shape is formed such that a taper angle is approximately 60 degrees with respect to the center axis.
2. The measuring device according to claim 1, wherein:
the first side surface and the second side surface are flat surfaces;
an end surface of the first cell disposed in the first cavity and the first side surface are substantially in the same plane; and
an end surface of the second cell disposed in the second cavity and the second side surface are substantially in the same plane.
3. The measuring device according to claim 2, wherein a distance between the first side surface and the second side surface is smaller than a length of the first side surface and the second side surface in the direction substantially orthogonal to the center axis.
4. The measuring device according to claim 2, wherein:
the first cell comprises a first main portion having a substantially cylindrical shape and a first flange portion formed at an end of the first main portion and having a substantially circular plate shape with a diameter greater than a diameter of the first main portion;
a first sealing member is disposed between the first cavity and the first main portion;
a first pressing member is disposed within the housing;
the first pressing member presses the first cell; and
end surfaces, on the first main portion side, of the first flange portion is pressed against the housing, and
wherein:
the second cell comprises a second main portion having a substantially cylindrical shape and a second flange portion formed at an end of the second main portion and having a substantially circular plate shape with a diameter greater than a diameter of the second main portion;
a second sealing member is disposed between the second cavity and the second main portion;
a second pressing member is disposed within the housing;
the second pressing member presses the second cell; and
end surfaces, on the second main portion side, of the second flange portion is pressed against the housing.
5. The measuring device according to claim 1, wherein a distance between the first side surface and the second side surface is smaller than a length of the first side surface and the second side surface in the direction substantially orthogonal to the center axis.
6. The measuring device according to claim 1,
wherein:
the first cell comprises a first main portion having a substantially cylindrical shape and a first flange portion formed at an end of the first main portion and having a substantially circular plate shape with a diameter greater than a diameter of the first main portion;
a first sealing member is disposed between the first cavity and the first main portion;
a first pressing member is disposed within the housing;
the first pressing member presses the first cell; and
end surfaces, on the first main portion side, of the first flange portion is pressed against the housing, and
wherein:
the second cell comprises a second main portion having a substantially cylindrical shape and a second flange portion formed at an end of the second main portion and having a substantially circular plate shape with a diameter greater than a diameter of the second main portion;
a second sealing member is disposed between the second cavity and the second main portion;
a second pressing member is disposed within the housing;
the second pressing member presses the second cell; and
end surfaces, on the second main portion side, of the second flange portion is pressed against the housing.
7. A measuring device comprising:
a housing comprising two surfaces facing away from each other, the housing being provided with a flow path structure, a first cavity, and a second cavity,
the flow path structure has two openings on the two surfaces respectively and comprises a first side surface and a second side surface facing each other,
the first cavity comprises one end opening on the first side surface,
the second cavity faces the first cavity across a center axis of the flow path structure and comprises one end opening on the second side surface;
a first cell disposed in the first cavity, made from a transparent material, and having a substantially cylindrical shape, both end surfaces of the first cell being flat surfaces;
a second cell disposed in the second cavity, made from a transparent material, and having a substantially cylindrical shape, both end surfaces of the second cell being flat surfaces;

a light emitting section configured to irradiate a hydraulic oil flowing in the flow path structure with light via the first cell in a direction substantially orthogonal to the center axis; and a light receiving section disposed facing the light irradiating section across the first cell, the flow path structure, and the second cell;

the first cavity and the second cavity having centers substantially coinciding with an optical axis being a center of light emitted from the light irradiating section, wherein a distance between the first side surface and the second side surface is smaller than a length of the first side surface and the second side surface in the direction substantially orthogonal to the center axis.

8. A measuring device comprising:

a housing comprising two surfaces facing away from each other, the housing being provided with a flow path structure, a first cavity, and a second cavity, the flow path structure has two openings on the two surfaces respectively and comprises a first side surface and a second side surface facing each other, the first cavity comprises one end opening on the first side surface, the second cavity faces the first cavity across a center axis of the flow path structure and comprises one end opening on the second side surface;

a first cell disposed in the first cavity, made from a transparent material, and having a substantially cylindrical shape, both end surfaces of the first cell being flat surfaces;

a second cell disposed in the second cavity, made from a transparent material, and having a substantially cylindrical shape, both end surfaces of the second cell being flat surfaces;

a light emitting section configured to irradiate a hydraulic oil flowing in the flow path structure with light via the first cell in a direction substantially orthogonal to the center axis; and a light receiving section disposed facing the light irradiating section across the first cell, the flow path structure, and the second cell;

the first cavity and the second cavity having centers substantially coinciding with an optical axis being a center of light emitted from the light irradiating section, wherein:

the first cell comprises a first main portion having a substantially cylindrical shape and a first flange portion formed at an end of the first main portion and having a substantially circular plate shape with a diameter greater than a diameter of the first main portion;

a first sealing member is disposed between the first cavity and the first main portion;

a first pressing member is disposed within the housing;

the first pressing member presses the first cell; and end surfaces, on the first main portion side, of the first flange portion is pressed against the housing, and wherein:

the second cell comprises a second main portion having a substantially cylindrical shape and a second flange portion formed at an end of the second main portion and having a substantially circular plate shape with a diameter greater than a diameter of the second main portion;

a second sealing member is disposed between the second cavity and the second main portion;

a second pressing member is disposed within the housing;

the second pressing member presses the second cell; and end surfaces, on the second main portion side, of the second flange portion is pressed against the housing.

* * * * *